United States Patent [19]

West

[11] Patent Number: 5,084,280
[45] Date of Patent: Jan. 28, 1992

[54] WOOD PRESERVATION COMPOSITION AND METHOD

[75] Inventor: Michael H. West, Senatobia, Miss.

[73] Assignee: Chapman Chemical Company, Memphis, Tenn.

[21] Appl. No.: 284,896

[22] Filed: Dec. 15, 1988

[51] Int. Cl.⁵ ............................................. A01N 59/14
[52] U.S. Cl. ..................................... 424/658; 424/657
[58] Field of Search ............... 424/140, 148, 630, 657, 424/658

[56] References Cited

U.S. PATENT DOCUMENTS 4,117,150 9/1978 Pommer et al. ..................... 514/471
4,656,060 4/1987 Krzyzewski ......................... 428/541

Primary Examiner—Frederick E. Waddell
Assistant Examiner—Zohreh A. Fay
Attorney, Agent, or Firm—Fred Philpitt

[57] ABSTRACT

A paste composition for preserving wood which contains as its only active wood preservation ingredients a mixture of a water-dispersible copper naphthenate and borax.

15 Claims, No Drawings

WOOD PRESERVATION COMPOSITION AND METHOD

TECHNICAL FIELD

This invention pertains to a method and composition for the preservation of wood.

BACKGROUND

There are many methods and compositions for preserving wood prior to the time the wood is put in use. Also, preservatives for treating wood in place are available on the market including both oil-based and water-based products. The oil-based products generally consist of petroleum oils, pentachlorophenol, and creosote. From the standpoint of toxicity and environmental pollution they are less than desirable. Furthermore, they provide only limited penetration into wood that is wet enough to support decay. The water-based products available often fail to provide adequate surface protection and are themselves composed of hazardous chemicals.

THE PRESENT INVENTION

The composition of this invention comprise as its essential ingredients both 20–80% by weight of a borate compound preferably 30–60%, (for internal wood preservation) and a 10–60% by weight (preferably 30–50%) of a water-dispersible copper naphthenate formulation for surface wood preservation. My composition also preferably includes clay, absorbent or a similar physical modifier, which together with water permit the formation of a paste.

The water-dispersible copper naphthenate formulations useful in the present invention are any of those registered by the U.S. Environmental Protection Agency for wood preservation. Any water-soluble borate may be used, but borax ($Na_2B_4O_7$-10 $H_2O$) is preferred because it is easy to formulate. Adequate borate should be present to treat the wood to be protected to levels of from 0.02 to 0.20 lbs$B_2O_3$/ft3 wood. Levels of copper naphthenate used in my composition are about from 0.5% to 2.0% weight percent as metallic copper based on the weight of the composition and these are levels approved by the EPA for surface treatments.

The compositions of this invention are preferably prepared by mixing the powdered or granular borate with a liquid copper naphthenate formulation, and then adding clay, water and/or other omponents as needed to produce a suitable paste.

The compositions of the present invention are primarily intended for use on wood already in place, such as poles, posts, sills, ties, toe plates, etc., and the present invention will be described primarily in connection with this use. Some of these poles may have been in place many years and the application of the compositions of the current invention thereto will add extra years to the life of the pole. Those poles which were poorly pretreated with inferior preservatives, may be again treated while in place. Poles which are removed from one location for setting in another location, usually at a different depth, can be advantageously treated with the compositions of the present invention.

Poles are most effectively treated with compositions of the present invention by applying a ⅛" to ½" thickness of the paste to the excavated pole at the ground line as well as somewhat above and below the ground line. The treated area is then wrapped with an impermeable material such as waxed paper or plastic. This impermeable material limits the composition being taken up by the soil and/or being leached from the pole to such an extent that an insufficient amount of preserving effect would be obtained. A ready-made package of the compositions of the current invention may be produced by depositing a layer of the preservative paste on a plastic sheet or on waxed paper.

EXAMPLES

To illustrate a suitable composition according to this invention the following ingredients were combined:

| Material | | Weight Percent |
| --- | --- | --- |
| Cunapsol-5 | (5% metallic copper equivalent water-dispersible copper naphthenate) | 40.0 |
| Borax | ($Na_2B_4O_7$-10 $H_2O$) | 40.0 |
| Clay | (Attagel 350) | 10.0 |
| Water | | 10.0 |

This formulation paste was brushed to a ¼" thickness on 22" wide waxed paper. The coated paper was then wrapped around the ends of ten green pole stubs and ten dry poles stubs so there was ¼" of the paste adjacent the surface of the wood. These poles stubs were of southern yellow pine and free from decay or previous preservation treatment. They were approximately six feet long and 10" to 12" in diameter. The paper with the ¼" layer of preservative paste was applied to each stub in such a manner that six inches of the treated paper and stub would be above the ground line and sixteen inches below the ground line. These stubs were placed in the ground with two feet of each stub below ground and four feet above ground. In the same manner ten untreated stubs and ten treated with an oil-based pentachlorophenol preservative paste, Pol Nu, were installed for comparative purposes.

After four years these stubs were thoroughly inspected and two each of the treated stubs were cut into quarters in order to verify penetration and effectiveness of treated chemicals. All of the untreated stubs had been destroyed by decay and/or insect attack. All treated stubs were in excellent condition at the ground line. Stubs treated with the composition of this invention were, to the top free of decay and insect attack. Borax was present throughout the stubs, treated green. The tops of the Pol-Nu treated stubs were attacked by decay and insects. The pentachlorophenol had migrated approximately half way up the stubs.

Another composition which was prepared in accordance with my invention included the following ingredients:

| | |
| --- | --- |
| Copper Hydro Nap (6% metallic copper equivalent water dispersable copper naphthenate) | 16.67% |
| Sodium Metaborate 4 $H_2O$ | 50.0% |
| Clay (Attagel 350) | 8.0% |
| Water | 25.33% |

This formulation produced a thick paste which is quite suitable for preserving wooden poles.

I claim:

1. A paste composition for preserving wood which contains as its only active wood preservation ingredients a mixture of 10–90% by weight of a water-dispersible copper naphthenate and 90-10% by weight of borax.

2. A paste composition according to claim 1 which contains 20-80% borax.

3. A paste composition according to claim 1 which contains 30-60% borax.

4. A paste composition according to claim 1 which contains 10-60% copper naphthenate.

5. A paste composition according to claim 1 which contains 30-50% copper naphthenate.

6. A paste composition according to claim 4 which contains 20-80% borax.

7. A paste composition according to claim 4 which contains 30-60% borax.

8. A paste composition according to claim 5 which contains 20-80% borax.

9. A paste composition according to claim 5 which contains 30-60% borax.

10. A paste composition according to claim 2 which contains 40% borax, 40% copper naphthenate, 10% clay and 10% water.

11. The method of preserving wood which comprises applying to the wood a paste composition which contains as its only active wood preservation ingredients a mixture of 10-90% by weight of a water-dispersible copper naphthenate and 90-10% by weight of borax and thereafter surrounding the coated area of the wood with an impermeable wrapper.

12. A method according to claim 11 wherein said mixture contains 20-80% borax.

13. A method according to claim 11 wherein said mixture contain 30-60% borax.

14. A method according to claim 11 wherein said mixture contains 10-60% copper naphthenate.

15. A method according to claim 11 wherein said mixture contain 30-50% copper naphthenate.

* * * * *